(12) United States Patent
Yuyama

(10) Patent No.: US 12,239,611 B2
(45) Date of Patent: Mar. 4, 2025

(54) DRUG AUDIT SUPPORT DEVICE, DRUG AUDIT SUPPORT SYSTEM, AND DRUG AUDIT METHOD

(71) Applicant: YUYAMA MFG. CO., LTD., Osaka (JP)

(72) Inventor: Hiroyuki Yuyama, Osaka (JP)

(73) Assignee: YUYAMA MFG. CO., LTD., Osaka (JP)

( * ) Notice: Subject to any disclaimer, the term of this patent is extended or adjusted under 35 U.S.C. 154(b) by 604 days.

(21) Appl. No.: 17/595,507

(22) PCT Filed: Jun. 4, 2020

(86) PCT No.: PCT/JP2020/022064
§ 371 (c)(1),
(2) Date: Nov. 18, 2021

(87) PCT Pub. No.: WO2020/246534
PCT Pub. Date: Dec. 10, 2020

(65) Prior Publication Data
US 2022/0142869 A1    May 12, 2022

(30) Foreign Application Priority Data
Jun. 7, 2019  (JP) ................................ 2019-107302

(51) Int. Cl.
*G16H 20/13* (2018.01)
*A61J 3/00* (2006.01)

(52) U.S. Cl.
CPC ............... *A61J 3/00* (2013.01); *G16H 20/13* (2018.01)

(58) Field of Classification Search
CPC .................................. A61J 3/00; G16H 20/13
See application file for complete search history.

(56) References Cited

U.S. PATENT DOCUMENTS

2003/0216831 A1  11/2003  Hart et al.
2008/0129496 A1  6/2008  Koblasz
(Continued)

FOREIGN PATENT DOCUMENTS

CN  109195568 A  1/2019
JP  2013048705 A  3/2013
(Continued)

OTHER PUBLICATIONS

International Preliminary Report on Patentability issued by the International Bureau of WIPO in relation to International Application No. PCT/JP2020/022064 dated Dec. 7, 2021 (5 pages) along with English language translation (5 pages).
Supplementary European Search Report issued by the European Patent Office in relation to European Application No. 20 81 8116 dated May 24, 2022 (2 pages).
(Continued)

*Primary Examiner* — Timothy R Waggoner
(74) *Attorney, Agent, or Firm* — Robert P. Michal, Esq.; Carter, DeLuca & Farrell LLP

(57) ABSTRACT

A drug inspection assisting apparatus for assisting an inspection of drugs collected by a drug collecting apparatus and/or by a manual operation, including: a plurality of drug inspection means, the drug inspection assisting apparatus being capable of implementing a plurality of drug inspection plans having different accuracies through selective implementation of the drug inspection means; an information acquiring means for acquiring first information and second information, the first information being information related to collection paths of drugs and/or devices involved in the collection of the drugs, the second information being information related to an operator who is involved in collection of drugs; and a plan selection means for selecting a certain drug inspection plan based on the first information and the second information, and the drug inspection plan selected by the plan selection means is implemented.

20 Claims, 8 Drawing Sheets

| FIRST INFORMATION | SECOND INFORMATION | | | |
|---|---|---|---|---|
| | PHARMACIST | | TECHNICIAN | |
| | EXPERIENCED | NOVICE | EXPERIENCED | NOVICE |
| A-TYPE CASSETTE WITH LOCK | SIMPLE | SIMPLE | MIDDLE | N/A |
| A-TYPE CASSETTE WITHOUT LOCK | MIDDLE | MIDDLE | HIGH | N/A |
| B-TYPE CASSETTE WITH LOCK | MIDDLE | MIDDLE | HIGH | N/A |
| B-TYPE CASSETTE WITHOUT LOCK | MIDDLE | MIDDLE | HIGH | N/A |
| SEMI-VARIABLE A-TYPE CASSETTE WITH LOCK | HIGH → SIMPLE | HIGH → SIMPLE | HIGH → SIMPLE | N/A |
| SEMI-VARIABLE A-TYPE CASSETTE WITHOUT LOCK | HIGH → MIDDLE | HIGH → MIDDLE | HIGH → MIDDLE | N/A |
| MANUAL DISTRIBUTION PORTION | HIGH | HIGH | N/A | N/A |

HIGH: UPPER-GRADE INSPECTION PLAN
MIDDLE: MIDDLE-GRADE INSPECTION PLAN
SIMPLE: SIMPLE INSPECTION PLAN
HIGH → SIMPLE: UPPER-GRADE INSPECTION PLAN FIRST, AND THEN SIMPLE INSPECTION PLAN AFTER ELAPSE OF TIME
HIGH → MIDDLE: UPPER-GRADE INSPECTION PLAN FIRST, AND THEN MIDDLE-GRADE INSPECTION PLAN AFTER ELAPSE OF TIME
N/A: VISUAL INSPECTION

(56) References Cited

U.S. PATENT DOCUMENTS

| | | | |
|---|---|---|---|
| 2016/0114925 A1 | 4/2016 | Yuyama et al. | |
| 2016/0343151 A1* | 11/2016 | Koike | G01B 11/02 |
| 2017/0008655 A1* | 1/2017 | Amano | B65H 16/103 |
| 2017/0301087 A1* | 10/2017 | Yuyama | A61J 1/03 |
| 2017/0305589 A1 | 10/2017 | Yuyama et al. | |
| 2020/0010224 A1 | 1/2020 | Koike et al. | |
| 2021/0019870 A1* | 1/2021 | Hellenbrand | G06T 7/80 |
| 2021/0205179 A1* | 7/2021 | Amano | B07C 5/342 |

FOREIGN PATENT DOCUMENTS

| | | | | |
|---|---|---|---|---|
| TW | 201213211 | * | 4/2012 | A61J 3/00 |
| WO | 2014129526 A1 | | 8/2014 | |
| WO | 2016047295 A1 | | 3/2016 | |
| WO | 2016047569 A1 | | 3/2016 | |

OTHER PUBLICATIONS

International Search Report issued by the Japanese Patent Office acting as the International Searching Authority in relation to International Application No. PCT/JP2020/022064 dated Jul. 28, 2020 (3 pages) along with English language translation (2 pages).

Written Opinion of the International Searching Authority issued by the Japanese Patent Office acting as the International Searching Authority in relation to International Application No. PCT/JP2020/022064 dated Jul. 28, 2020 (4 pages) along with English language machine translation (3 pages).

Office Action issued by the The State Intellectual Property Office of People's Republic of China in relation to Chinese Application No. 202080032300.1, dated Jul. 25, 2024 (9 pages) along with English Translation (12 pages) 21 total pages.

* cited by examiner

FIG. 11

| FIRST INFORMATION | SECOND INFORMATION | | | |
|---|---|---|---|---|
| | PHARMACIST | | TECHNICIAN | |
| | EXPERIENCED | NOVICE | EXPERIENCED | NOVICE |
| A-TYPE CASSETTE WITH LOCK | SIMPLE | SIMPLE | MIDDLE | N/A |
| A-TYPE CASSETTE WITHOUT LOCK | MIDDLE | MIDDLE | HIGH | N/A |
| B-TYPE CASSETTE WITH LOCK | MIDDLE | MIDDLE | HIGH | N/A |
| B-TYPE CASSETTE WITHOUT LOCK | MIDDLE | MIDDLE | HIGH | N/A |
| SEMI-VARIABLE A-TYPE CASSETTE WITH LOCK | HIGH → SIMPLE | HIGH → SIMPLE | HIGH → SIMPLE | N/A |
| SEMI-VARIABLE A-TYPE CASSETTE WITHOUT LOCK | HIGH → MIDDLE | HIGH → MIDDLE | HIGH → MIDDLE | N/A |
| MANUAL DISTRIBUTION PORTION | HIGH | HIGH | N/A | N/A |

HIGH: UPPER-GRADE INSPECTION PLAN

MIDDLE: MIDDLE-GRADE INSPECTION PLAN

SIMPLE: SIMPLE INSPECTION PLAN

HIGH → SIMPLE: UPPER-GRADE INSPECTION PLAN FIRST, AND THEN SIMPLE INSPECTION PLAN AFTER ELAPSE OF TIME

HIGH → MIDDLE: UPPER-GRADE INSPECTION PLAN FIRST, AND THEN MIDDLE-GRADE INSPECTION PLAN AFTER ELAPSE OF TIME

N/A: VISUAL INSPECTION

DRUG AUDIT SUPPORT DEVICE, DRUG AUDIT SUPPORT SYSTEM, AND DRUG AUDIT METHOD

CROSS-REFERENCE TO RELATED APPLICATIONS

This application is a National Phase Entry under 35 U.S.C. 371 of PCT International Application No. PCT/JP2020/022064 filed Jun. 4, 2020, which claims priority to Japan Patent Application No. 2019-107302, filed Jun. 7, 2019, the disclosure of each of these applications is expressly incorporated herein by reference in their entirety.

TECHNICAL FIELD

The present invention relates to a drug inspection assisting apparatus which is to be used for inspecting whether drugs have been collected as prescribed. Further, the present invention relates to a drug inspection assisting system including the drug inspection assisting apparatus and a drug collecting apparatus. Further, the present invention relates to a drug inspection method.

BACKGROUND ART

In a dispensing pharmacy or the like, drugs are collected based on a prescription issued by a doctor, and an inspection is performed to check whether the drugs have been collected as prescribed. After that, the drugs are provided to a patient or the like.

In Patent Literature 1, there is disclosed a drug inspection assisting apparatus for assisting an inspection performed by a pharmacist.

Further, in Patent Literature 1, a drug packaging apparatus is disclosed. The drug packaging apparatus includes a plurality of drug cassettes accommodated therein, and a predetermined number of solid preparations are automatically discharged from the drug cassettes. The drug packaging apparatus includes a drug packing device, and the drugs discharged from the drug cassettes are packed for each administration.

CITATION LIST

Patent Literature

Patent Literature 1: WO 2014/129526 A1
Patent Literature 2: WO 2016/47569 A1

SUMMARY OF INVENTION

Technical Problem

The inspection operation performed by a pharmacist is a final checking operation for providing drugs to a patient or the like. Such inspection operation is the most important among a series of preparation actions and needs to be performed carefully.

Meanwhile, a drug inspection is the work that needs time and effort.

For example, even when the drug inspection assisting apparatus as disclosed in Patent Literature 1 is used, considerable time is required for completing the inspection.

The present invention gives focus on the problem described above, and has an object to develop a drug inspection assisting apparatus which is capable of shortening the time required for an inspection while maintaining the accuracy of the inspection. Further, the present invention has an object to develop a drug inspection assisting system and a drug inspection method which solve the same problem.

Solution to Problem

In order to solve the problem described above, according to one aspect, there is provided a drug inspection assisting apparatus for assisting an inspection of drugs collected by a drug collecting apparatus and/or by a manual operation, including: a plurality of drug inspection means, the drug inspection assisting apparatus being capable of implementing a plurality of drug inspection plans having different accuracies; an information acquiring means for acquiring first information and second information, the first information being information related to collection paths of drugs and/or devices involved in the collection of the drugs, the second information being information related to an operator who is involved in collection of drugs; and a plan selection means for selecting a certain drug inspection plan from among the plurality of drug inspection plans based on the first information and the second information, wherein, in accordance with the drug inspection plan selected by the plan selection means, inspection by one or a plurality of the drug inspection means are implemented.

In the drug inspection plan, the drug inspection means to be used is selected. In the drug inspection plan, one drug inspection means or a plurality of drug inspection means are to be used.

Implementing the drug inspection plan means that an inspection is performed with use of the drug inspection means included in the drug inspection plan.

For plan selection, information other than the first information and the second information may be included.

In the aspect described above, it is preferred that the drug collecting apparatus have a function of accommodating a plurality of kinds of drugs inside and automatically dispensing desired drugs, and the second information include information related to an operator who is involved in an operation of accommodating the drugs into the drug collecting apparatus.

In each of the aspects described above, it is preferred that the second information include at least one of information (A1) and information (A2), where:
 (A1) presence or absence of a public qualification; and
 (A2) amount of experience.

Further, in order to solve the problem described above, according to another aspect, there is provided a drug inspection assisting apparatus for assisting an inspection of drugs collected by a drug collecting apparatus and/or by a manual operation, including: a plurality of drug inspection means, the drug inspection assisting apparatus being capable of implementing a plurality of drug inspection plans having different accuracies; an information acquiring means for acquiring first information, the first information being information related to collection paths of drugs and/or devices involved in the collection of the drugs; and a plan selection means for selecting a certain drug inspection plan from among the plurality of drug inspection plans based on the first information, wherein, in accordance with the drug inspection plan selected by the plan selection means, inspection by one or a plurality of the drug inspection means are implemented.

For plan selection, information other than the first information may be included.

In each of the aspects described above, it is preferred that the first information include information (B1), where:
(B1) whether or not all of the collected drugs have been collected with use of a drug collecting apparatus, and the drug correcting apparatus has a function of accommodating a plurality of kinds of drugs inside and automatically dispensing desired drugs.

In each of the aspects described above, it is preferred that the first information include information (C1), where:
(C1) whether or not all of the collected drugs have been accommodated in the drug collecting apparatus.

In each of the aspects described above, it is preferred that the first information include information (D1), where:
(D1) whether or not at least part of the collected drugs have been collected with use of the drug collecting apparatus, and the drug collecting apparatus includes a manual distribution portion, and the manual distribution portion includes a plurality of drug charging portions so that a predetermined number of drugs are charged into the drug charging portion by a manual operation of an operator, and at least part of the collected drugs are drugs having been collected via the manual distribution portion.

In each of the aspects described above, the following is preferred. The collected drugs are collected with use of a drug collecting apparatus, the drug collecting apparatus includes a manual distribution portion and a plurality of drug cassette mounting portions, the manual distribution portion includes a plurality of drug charging portions, and a predetermined number of drugs are charged into the drug charging portions by manual operation of an operator, at least two kinds of drug cassettes are mounted to the drug cassette mounting portion, and at least one kind of the drug cassette is a fixed cassette to be used exclusively for a certain drug, and at least another one kind of the drug cassette is a general-purpose cassette to be used for a plurality of kinds of drugs, and the first information includes distinctions (E1) to (G1), where:
(E1) all of the collected drugs are drugs having been accommodated in the fixed cassette;
(F1) part or all of the collected drugs pass through the general-purpose cassette, and all of other drugs have been accommodated in the fixed cassette; and
(G1) part or all of the collected drugs pass through the manual distribution portion.

In each of the aspects described above, it is preferred that the first information include information as to whether it is satisfied a requirement (H1), where:
(H1) all of the collected drugs have been collected with use of the drug collecting apparatus, and the drug collecting apparatus has a plurality of drug cassettes mounted thereto and has a function of accommodating a plurality of kinds of drugs inside the drug cassettes and automatically dispensing desired drugs.

In the aspect described above, it is preferred that the first information include information (I1), where:
(I1) structural distinction of the drug cassettes.

In the aspect described above, it is preferred that the drug cassettes include a drug charging portion configured to charge drugs, and the structural distinction include the drug charging portion which is capable of being locked and the drug charging portion which is incapable of being locked.

In each of the aspects described above, it is preferred that the structural distinction include the drug cassette adaptable to a large number of kinds of drugs and the drug cassette adaptable to a small number of kinds of drugs.

In each of the aspects described above, it is preferred that the first information include information (J1), where:
(J1) usage distinction of the drug cassette.

In the aspect described above, it is preferred that the usage distinction include information that the drug cassettes include a fixed cassette to be used exclusively for a certain drug and a general-purpose cassette to be used for a plurality of kinds of drugs.

In each of the aspects described above, the following is preferred. The first information and/or the second information includes certain specific information, and a certain drug inspection plan is selected based on the first information and/or the second information, and the drug inspection plan is implemented. After that, the same drug inspection plan is selected a plurality of times based on the first information and/or the second information including the specific information, and the drug inspection plan is implemented a plurality of times, and as a result, under a condition in which no error has been found in the collected drugs in all of the implementations, plan change control for correcting the accuracy of the drug inspection plan downward is implemented.

In each of the aspects described above, the following is preferred. Information acquired by the information acquiring means include certain specific information, and a certain drug inspection plan is selected based on the information, and, after that, the same drug inspection plan is selected a plurality of times based on the information including the specific information, thus the drug inspection plan is implemented, and the drug inspection plan is implemented a plurality of times, and as a result, under a condition in which no error has been found in the collected drugs in all of the implementations, plan change control for correcting the accuracy of the drug inspection plan downward is implemented.

In a drug inspection assisting system according to an aspect, the following is preferred. A drug inspection assisting system includes: the drug inspection assisting apparatus according to each of the aspects described above; and a drug collecting apparatus, wherein the drug collecting apparatus includes a manual distribution portion and a plurality of drug cassette mounting portions, wherein the manual distribution portion includes a plurality of drug charging portions, and a predetermined number of drugs are charged into the drug charging portions by manual operation of an operator, wherein at least two kinds of drug cassettes are mounted to the drug cassette mounting portion, and at least one kind of the drug cassette is a fixed cassette to be used exclusively for a certain drug, and at least another one kind of the drug cassette is a general-purpose cassette to be used for a plurality of kinds of drugs.

According to an aspect, there is provided a drug inspection assisting method for assisting, with use of a drug inspection assisting apparatus, an inspection of drugs collected by a drug collecting apparatus and/or by a manual operation of an operator, wherein the drug inspection assisting apparatus comprises a plurality of drug inspection means, and is capable of implementing drug inspection plans having different accuracies, wherein the drug inspection plan is selected based on first information and second information, wherein, in accordance with the drug inspection plan, an inspection by one or a plurality of the drug inspection means is implemented, wherein the first information is information related to collection paths of drugs and/or devices involved in the collection of the drugs, and wherein the second information is information related to an operator who is involved in collection of drugs.

Advantageous Effects of Invention

When the drug inspection assisting apparatus or the like according to the present invention is used, the time required for inspection can be shortened while maintaining the accuracy of the inspection.

BRIEF DESCRIPTION OF DRAWINGS

FIG. 11 is a selection table for drug inspection plans.

DESCRIPTION OF EMBODIMENTS

Figure 1:
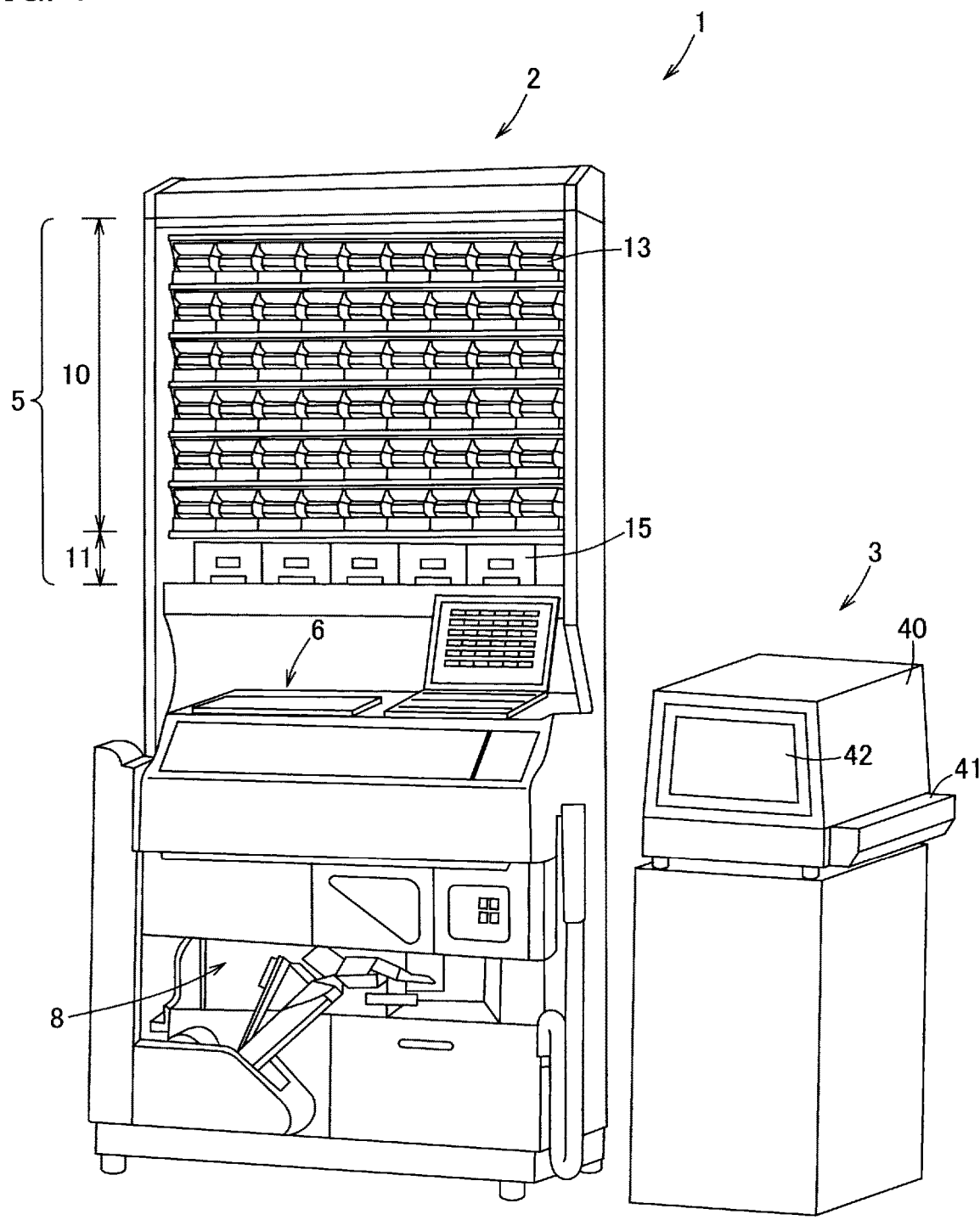
FIG. 1 is a front view of a drug inspection assisting system according to an embodiment of the present invention.

Now, an embodiment of the present invention is further described. A drug inspection assisting system 1 according to this embodiment includes a drug dispensing apparatus (drug collecting apparatus) 2 and a drug inspection assisting apparatus 3.

The drug dispensing apparatus 2 is roughly divided into a cassette mounting portion 5, a manual distribution portion 6, and a drug packing portion 8.

Further, the cassette mounting portion 5 includes a fixed-cassette mounting area 10 and a general-purpose-cassette mounting area 11.

In the fixed-cassette mounting area 10, A-type cassettes (fixed cassettes) 13 are mounted. Further, in the general-purpose-cassette mounting area 11, B-type cassettes (general-purpose cassettes) 15 are mounted.

In the drug dispensing apparatus 2, a plurality of kinds of drug cassettes are used.

The drug cassettes are classified, in terms of structure, into the A-type cassette 13 and the B-type cassette 15. Further, a variable A-type cassette can also be used.

Further, the drug cassettes include, in terms of structure, those having a locking function and those having no locking function.

Further, the drug cassettes are classified, in terms of usage, into a fixed cassette and a general-purpose cassette. The A-type cassette 13 can be used only as a fixed cassette. The B-type cassette 15 is mainly used as a general-purpose cassette, but can be used also as a fixed cassette.

A semi-variable A-type cassette is mainly used as a fixed cassette, but can be used also as a general-purpose cassette.

Figure 2:
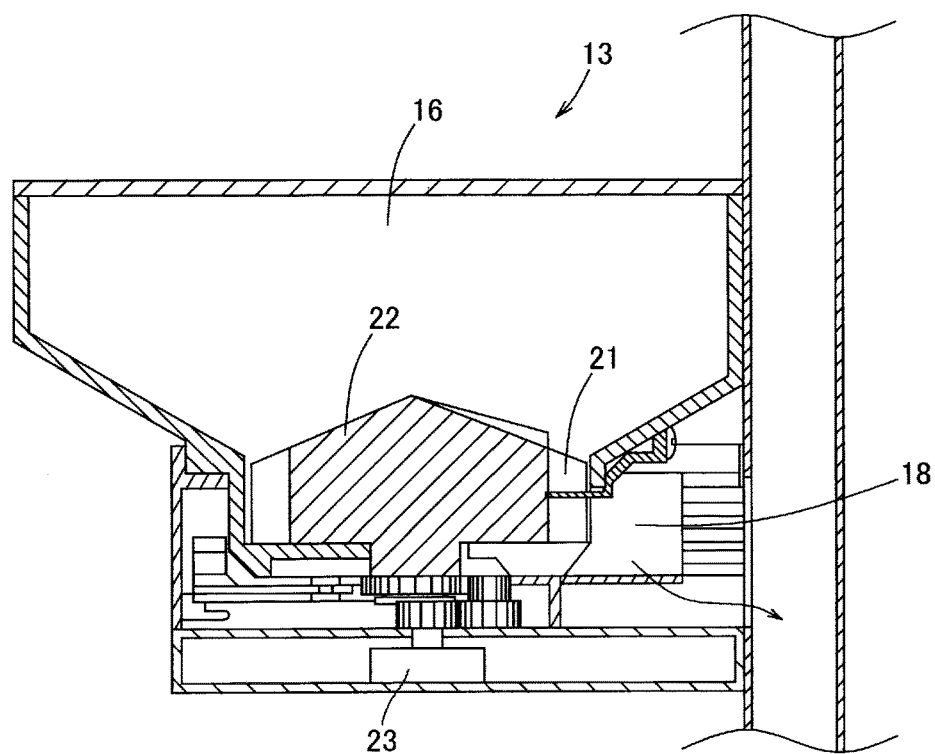
FIG. 2 is a sectional view of an A-type cassette (fixed cassette).
Figure 3:
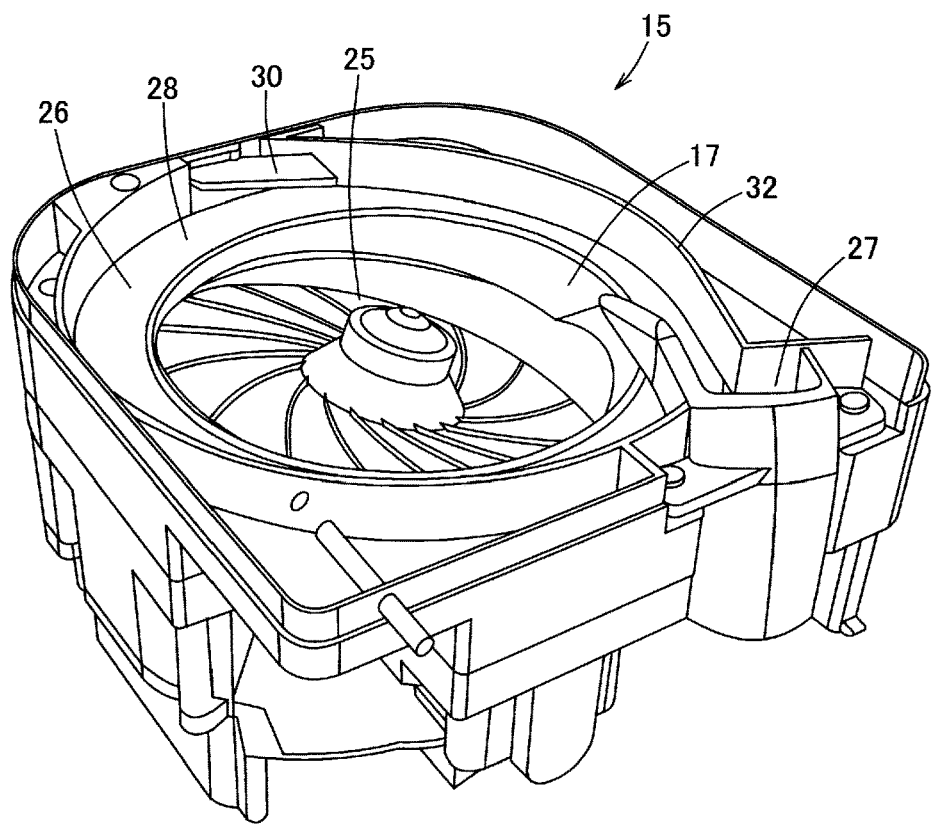
FIG. 3 is a perspective view of a B-type cassette (general-purpose cassette).

As illustrated in FIG. 2 and FIG. 3, the A-type cassette 13 and the B-type cassette 15 include drug accommodating portions 16 and 17, respectively. The drug accommodating portions 16 and 17 are capable of accommodating a large number of solid drugs such as tablets and capsules.

The A-type cassette 13 and the B-type cassette 15 have a function of discharging the drugs accommodated in the respective drug accommodating portions 16 and 17 one by one.

Further, the drug dispensing apparatus 2 includes a counting means (not shown) and is capable of counting the number of solid drugs discharged from the A-type cassette 13 and the B-type cassette 15.

The drugs having been discharged from the A-type cassette 13 and the B-type cassette 15 fall through a drug-dispensing passage (not shown) provided on a back side and are delivered to the drug packing portion 8 provided at a lower part. Then, the drugs are packed for each administration in the drug packing portion 8.

The A-type cassette 13 and the B-type cassette 15 are different in structure and have different functions. Further, in this embodiment, the A-type cassette 13 and the B-type cassette 15 are different also in usage.

The A-type cassette 13 includes a rotor 22 built in the drug accommodating portion 16 as illustrated in FIG. 2. The rotor 22 has a vertical groove-like pocket 21 for accommodating tablets.

When the rotor 22 provided inside the drug accommodating portion 16 is rotated by a motor 23, the drugs accommodated inside the drug accommodating portion 16 are discharged one by one.

In the A-type cassette 13, the pocket 21 formed in the rotor 22 forms a part of a dispensing passage, and the drugs fall into the pocket 21 and are discharged from a drug discharge port 18. The A-type cassette 13 can be referred to also as a cassette of a dispensing-passage fixed type, and a size of the pocket (dispensing passage) 21 cannot essentially be changed. Thus, a size of the drug which can be discharged depends on the size of the pocket 21.

Thus, the A-type cassette 13 can discharge only solid drugs having a size and a shape which fall within certain ranges.

The semi-variable A-type cassette (not shown) is obtained by modifying the cassette such that sizes of, for example, the pocket 21 and the drug discharge port 18 can be changed. The semi-variable A-type cassette can be referred to also as a cassette of a dispensing-passage semi-variable type.

Meanwhile, the B-type cassette 15 includes, as illustrated in FIG. 3, the drug accommodating portion 17, an inner rotary body 25, and an outer rotary body 26. The drug accommodating portion 17 accommodates a large number of tablets. The inner rotary body 25 and the outer rotary body 26 are provided in the drug accommodating portion.

The B-type cassette 15 is adaptable to tablets and capsule drugs having various shapes and structures, and is capable of discharging one or a plurality of the tablets and capsule drugs at a time.

The inner rotary body 25 is rotated by a motor (not shown). Further, the inner rotary body 25 rises and falls to give drugs to the outer rotary body 26.

The outer rotary body 26 is provided on an upper part side of the drug accommodating portion 17. An upper end portion of the inner rotary body 25 described above is located on the same horizontal plane as the outer rotary body 26.

The outer rotary body 26 is also rotated by a motor (not shown).

A part of the outer rotary body 26 is continuous with a drug discharge port 27 for discharging tablets from the drug accommodating portion 17. A height regulating member 30 and a width regulating member 32 are arranged on a dispensing passage 28 formed by the outer rotary body 26.

The height regulating member 30 described above is configured to regulate a height above a conveyance surface of the outer rotary body 26. The height regulating member 30 is configured to regulate a height of objects that pass through this part. The height regulating member 30 is configured to regulate a size in a height direction of tablets which can be conveyed to the drug discharge port 27 by the outer rotary body 26.

Meanwhile, the width regulating member 32 protrudes from lateral sides of the outer rotary body 26 toward an area (dispensing passage 28) of the outer rotary body 26 and temporarily narrows the width of the dispensing passage 28 of the outer rotary body 26. The width regulating member 32 is configured to regulate a size in a width direction of tablets which can be conveyed to the drug discharge port 27 by the outer rotary body 26.

In the B-type cassette 15, when a height and a width thereof correspond to a height and a width of one tablet accommodated in the drug accommodating portion 17, one tablet can be dispensed at a time.

Further, in the B-type cassette 15, through operation on a member that is not shown, the height regulating member 30 and the width regulating member 32 are moved so that the size in the height direction and the size in the width direction of the tablets which can be conveyed can be changed.

Thus, the B-type cassette 15 is adaptable to various sizes.

The B-type cassette 15 can be referred to also as a cassette of a dispensing-passage variable type.

In the B-type cassette 15, the height regulating member 30 and the width regulating member 32 are moved so that the size in the height direction and the size in the width direction of the tablets which can be conveyed can be changed. Thus, as compared to the A-type cassette 13, the B-type cassette 15 is adaptable to a wider variety of solid drugs.

When the structures of the cassettes are compared, the A-type cassette 13 and the semi-variable A-type cassette include the rotor 22 inside, and the pocket 21 of the rotor 22 forms a part of the dispensing passage, thereby regulating the size of drugs passing therethrough.

In contrast, the B-type cassette 15 includes the height regulating member 30 and the width regulating member 32, thereby regulating the size of drugs passing therethrough.

When functions of the cassettes are compared, the A-type cassette 13 can discharge only drugs having a certain shape. In contrast, the B-type cassette 15 can discharge drugs of any size. The semi-variable A-type cassette is similar to the B-type cassette 15 in an applicable range of a shape of the drugs.

That is, the A-type cassette 13 can discharge only solid drugs having a size and a shape which fall within certain ranges, whereas the B-type cassette 15 can discharge, through adjustment of the height regulating member 30 and the width regulating member 32, larger drugs or smaller drugs, or drugs having a wide variety of shapes such as capsules. Further, similarly to the B-type cassette 15, the semi-variable A-type cassette can also discharge drugs having a wide variety of shapes through adjustment of a width (circumferential direction), a height, and a thickness (radial direction) of the pocket of the rotor 22.

The A-type cassette 13 has a smaller variety in kinds of applicable drugs. In contrast, the B-type cassette 15 has a larger variety in kinds of applicable drugs.

In this embodiment, the A-type cassettes 13 are mounted in the fixed-cassette mounting area 10, and the B-type cassettes 15 are mounted in the general-purpose-cassette mounting area 11. The A-type cassette 13 mounted in the fixed-cassette mounting area 10 is referred to as "fixed cassette" in terms of usage, and the B-type cassette 15 mounted in the general-purpose-cassette mounting area 11 is referred to as "general-purpose cassette" in terms of usage.

The fixed cassette (A-type cassette 13) mounted in the fixed-cassette mounting area 10 is used exclusively for a certain drug. For example, a medicine A is always accommodated in one fixed cassette (A-type cassette 13), and no other drug is accommodated. Further, a medicine B is always accommodated in another one fixed cassette (A-type cassette 13), and no other drug is accommodated.

In contrast, a plurality of kinds of drugs are accommodated and used in the general-purpose cassette (B-type cassette 15) mounted in the general-purpose-cassette mounting area 11.

In this embodiment, five general-purpose cassettes (B-type cassettes 15) are installed, and different kinds of drugs may be accommodated and used in each of the general-purpose cassettes.

For example, it is assumed that prescribed drugs include the medicine A, the medicine B, and a medicine C, and that a fixed cassette (A-type cassette 13) for the medicine A and a fixed cassette (A-type cassette 13) for the medicine B are provided but no cassette for the medicine C is provided in the fixed-cassette mounting area 10.

In this case, the medicine C is filled into any one of the general-purpose cassettes (B-type cassettes 15), and the medicine C is discharged from the B-type cassette 15.

Further, when no fixed cassette for a medicine D is provided but a prescription includes the medicine D, the medicine D is filled into any one of the general-purpose cassettes (B-type cassettes 15), and the medicine D is discharged from the B-type cassette 15.

Thus, various kinds of drugs are filled into the general-purpose cassettes (B-type cassettes 15) depending on occasions.

Further, the A-type drug cassettes 13 and the B-type cassettes 15 include those having a locking function and those having no locking function.

An A-type cassette 13L with a lock and a B-type cassette 15L with a lock having a locking function include a lid member configured to close a solid-preparation accommodating portion and are provided with a lid locking means for holding the lid member in a locked state.

The "lid member in a locked state" corresponds to a state in which the lid member is prevented from being opened. The lid member "in the locked state" cannot be opened without using equipment or performing complicated operation.

Further, the A-type cassette 13L with a lock and the B-type cassette 15L with a lock employed in this embodiment can be filled with drugs only when the cassette is placed on a certain placement table or the like and a person qualified for unlocking performs authentication and certain operation.

The A-type cassette 13L with a lock and the B-type cassette 15L with a lock have the same locking mechanism. Thus, the B-type cassette 15L with a lock (hereinafter simply referred to as "B-type cassette 15L") is described as a representative.

Figure 5:
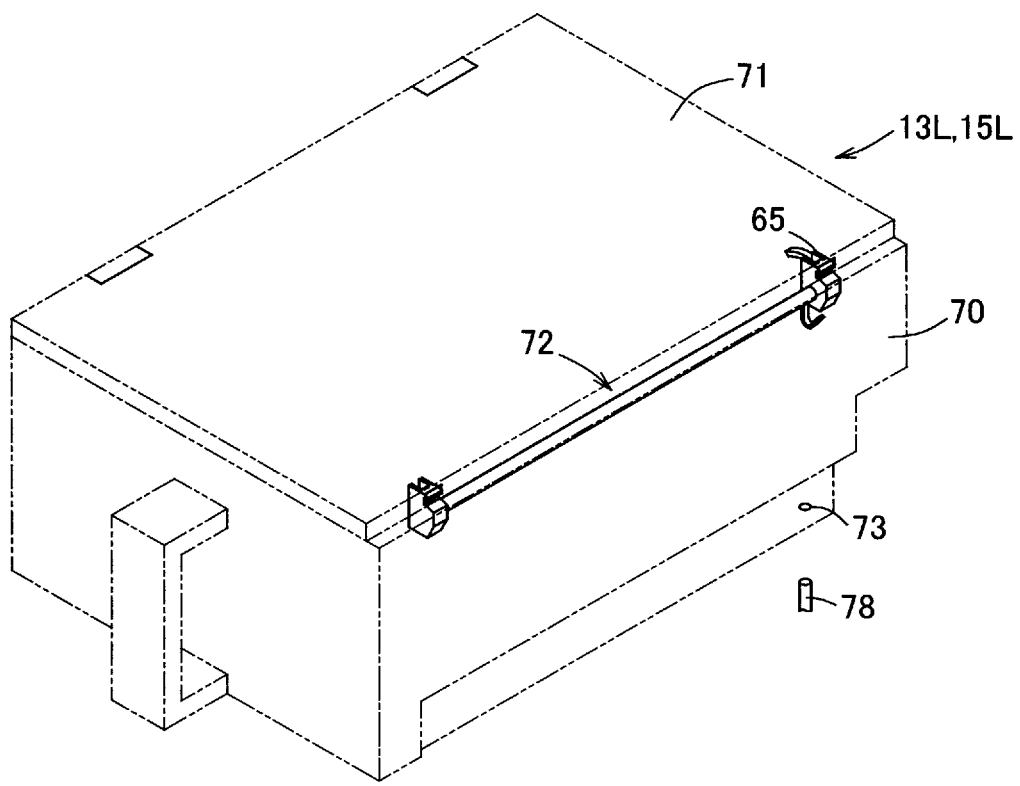
FIG. 5 is an explanatory view for conceptually illustrating a lid locking means built in a drug cassette, and is an illustration of a case in which the lid locking means is in a locking state.
Figure 6:
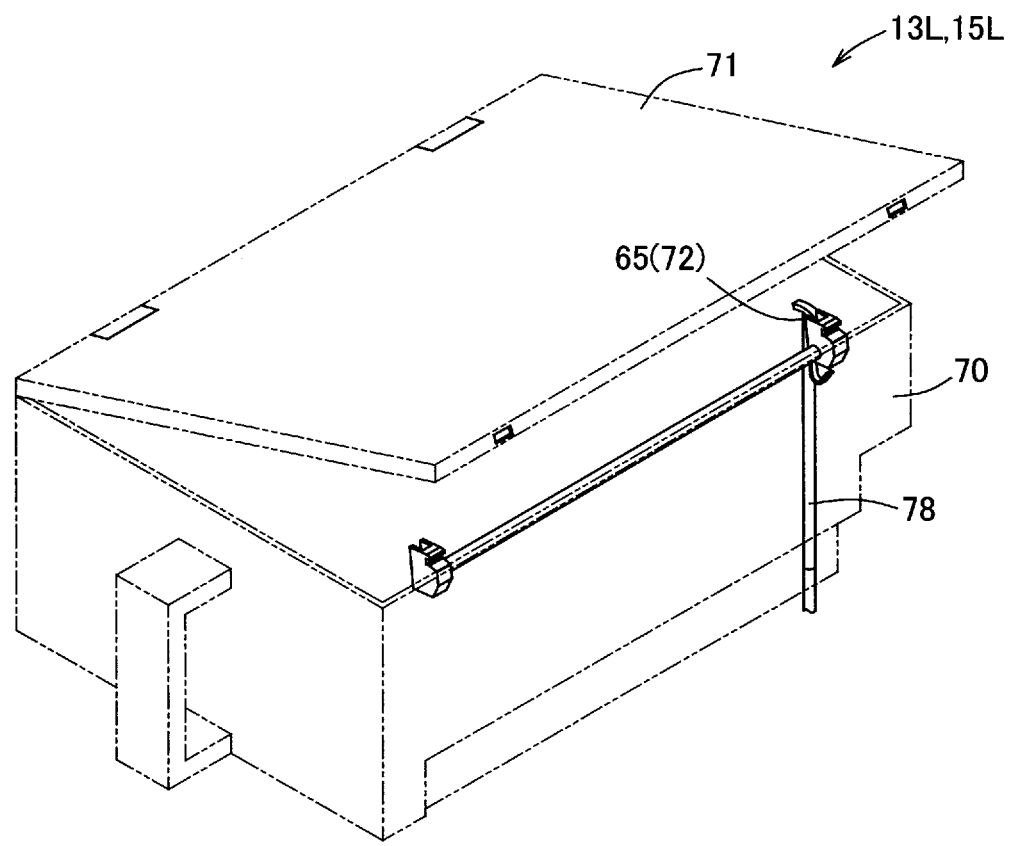
FIG. 6 is an explanatory view for conceptually illustrating the lid locking means built in a drug cassette, and is an illustration of a case in which the lid locking means is in an unlocking state.

As illustrated in FIG. 5 and FIG. 6, the B-type cassette 15L includes, inside a main body 70, a locking mechanism 72 for locking a lid member 71. The locking mechanism 72 is provided with an operation lever 65.

Further, a hole 73 is formed in a bottom surface of the main body 70 of the B-type cassette 15L.

Figure 7:
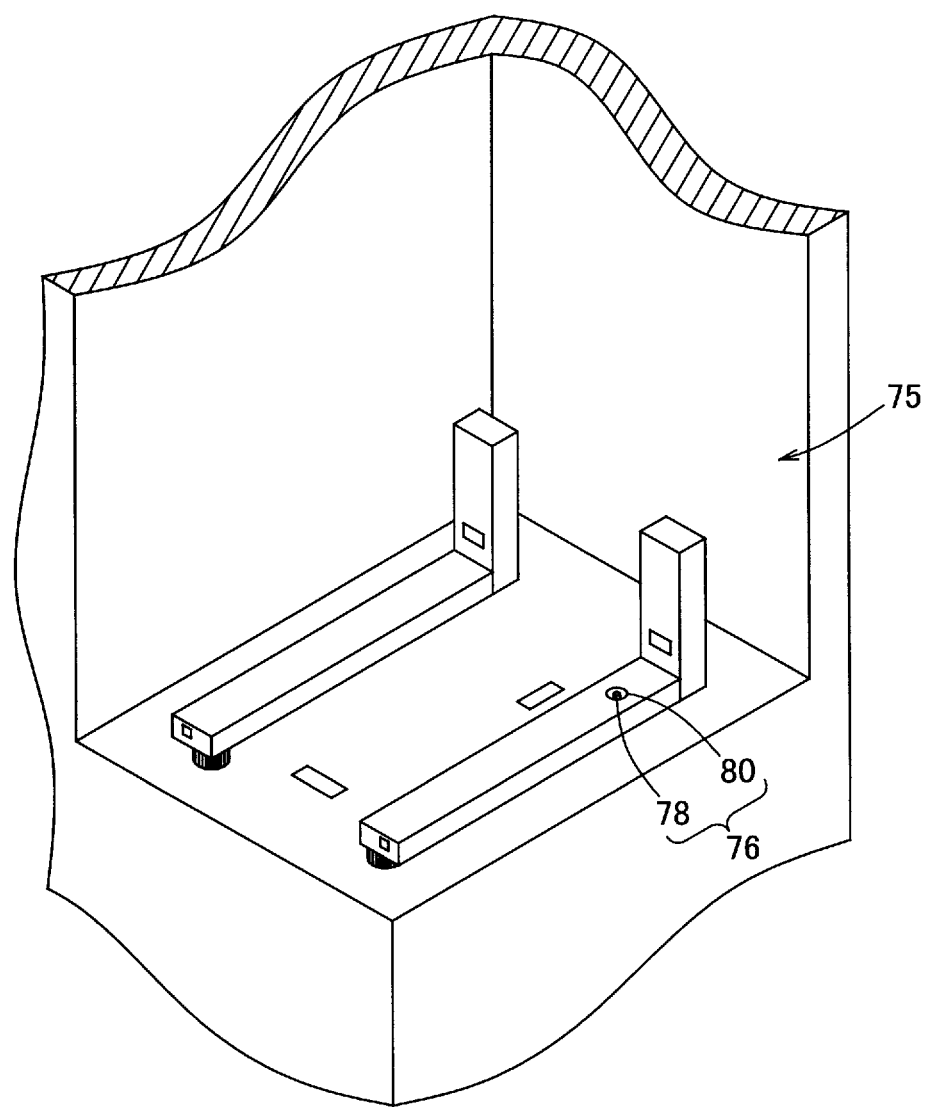
FIG. 7 is a perspective view of a cassette placement portion.
Figure 8:
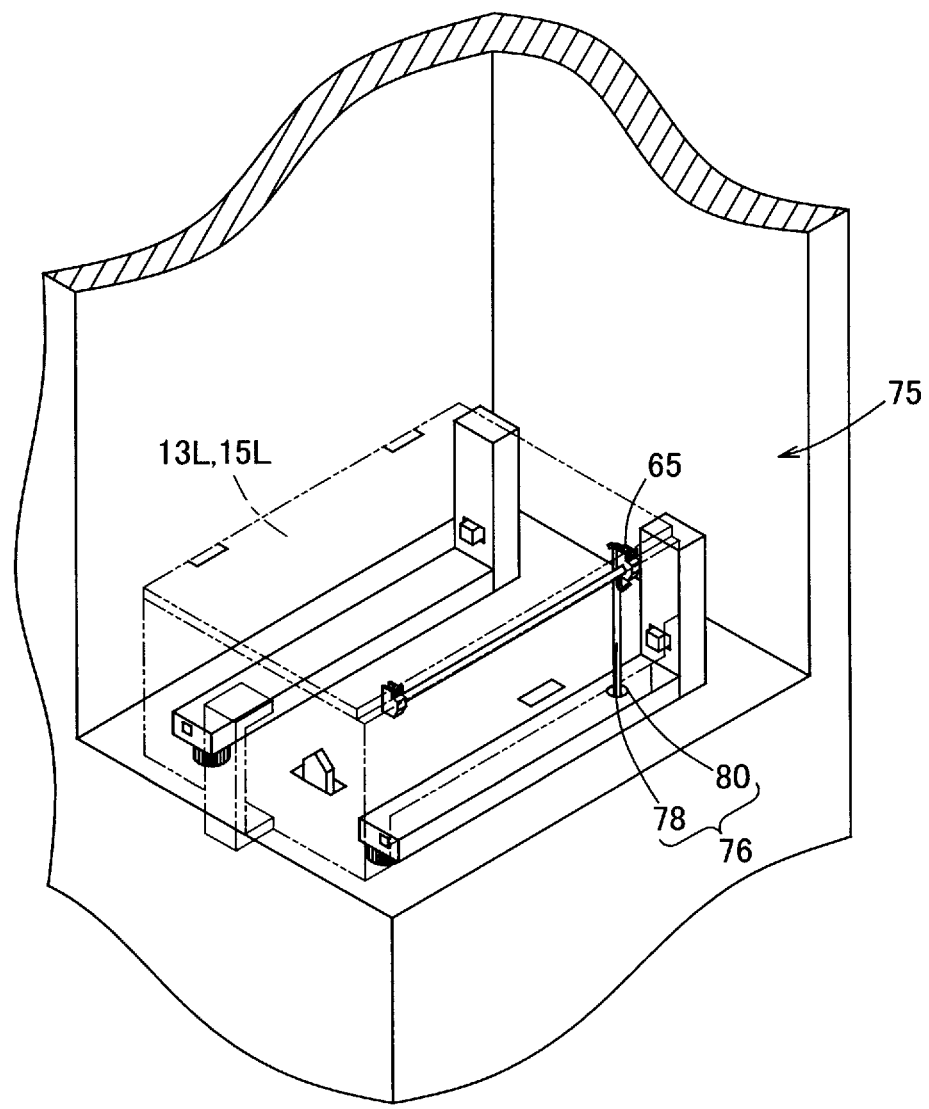
FIG. 8 is an explanatory view for illustrating a relationship between the cassette placement portion and the drug cassette in a state in which the drug cassette is mounted to the cassette placement portion.

A cassette placement portion 75 like the one illustrated in FIG. 7 and FIG. 8 is provided to the drug dispensing apparatus 2 or in the vicinity of the drug dispensing apparatus 2. The cassette placement portion 75 is a portion for temporarily placing (place) the B-type cassette 15L to supplement the B-type cassette 15L with drugs.

The cassette placement portion 75 is provided with a lid locking operation means 76. The lid locking operation means 76 includes a rod 78 as illustrated in FIG. 7 and FIG. 8. The rod 78 is always retreated in an opening 80 and projects vertically as needed.

In this embodiment, the rod 78 projects from the lid locking operation means 76 to be inserted through the hole 73 of the B-type cassette 15L. Then, the rod 78 passes through the hole 73 to operate the operation lever 65 of the locking mechanism 72, thereby unlocking the lid member 71.

Further, when the rod 78 separates away from the operation lever 65, the locking mechanism 72 returns to the locking state.

Figure 4:
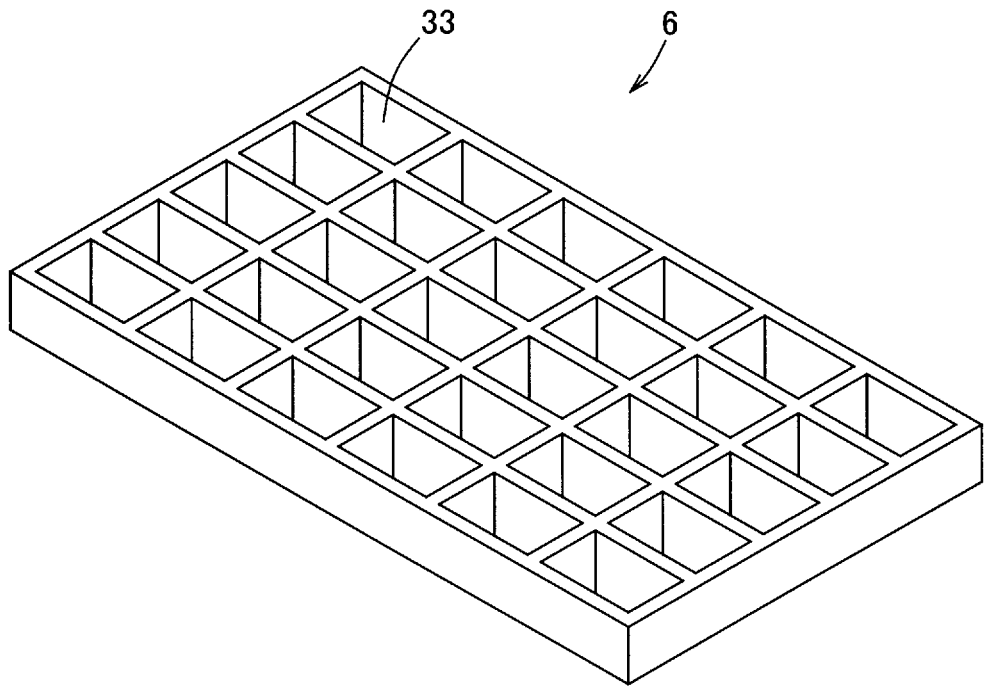
FIG. 4 is a perspective view of a manual distribution portion.

The manual distribution portion 6 is similar to publicly known manual distribution portions. As illustrated in FIG. 4, the manual distribution portion 6 includes a plurality of drug charging portions 33, and a predetermined number of drugs are charged into the drug charging portions 33 for each administration timing (morning, daytime, and night) by manual operation of an operator. Then, bottoms of the drug charging portions 33 open one after another, and the drugs provided in the drug charging portions 33 are caused to fall for each drug charging portion 33 and delivered to the drug packing portion 8 at a lower part.

Next, a method of use of the drug dispensing apparatus 2 is described.

In the drug dispensing apparatus 2 of this embodiment, the fixed cassettes (A-type cassettes 13) are filled with dedicated drugs, respectively.

The filling operation for drugs is performed by a pharmacist or the like or an operator who is called "technician." Specifically, the drugs are charged into the A-type cassette 13 from a drug bottle, and at the time of charging, a readable identification means such as a barcode or a two-dimensional code attached to the drug bottle is read with a code reader or the like. For the reading of the code or the like attached to the drug bottle, a reading device provided to the drug dispensing apparatus 2 and a portable reading terminal are used. In many cases, the portable reading terminal is used at the time of selecting a drug bottle from a shelf or the like, and the reading device provided to the drug dispensing apparatus 2 is used at the time of actually transferring the drugs from the drug bottle to the A-type cassette 13.

Further, data written in a radio frequency identification (RFID) or the like attached to the A-type cassette 13 is read, and it is checked whether or not the A-type cassette 13 is appropriate to be filled with the drugs accommodated in the drug bottle.

Further, information as to an operator who has performed the filling is recorded. This information is recorded in an upper apparatus (not shown) or the drug dispensing apparatus 2.

Drugs are filled into some of the general-purpose cassettes (B-type cassettes 15). The operation performed at this time is the same as that of the case in which drugs are filled into the fixed cassette (A-type cassette 13).

Some of the general-purpose cassettes (B-type cassettes 15) are empty.

The drug dispensing apparatus 2 is configured to dispense drugs in accordance with prescription data and pack the drugs for each administration.

When all of drugs included in prescription data are provided in the drug dispensing apparatus 2, and all of those drugs are provided in the fixed cassettes (A-type cassettes 13) mounted in the fixed-cassette mounting area 10, desired drugs are discharged from the fixed cassettes (A-type cassettes 13) and packed for each administration.

When all of drugs included in prescription data are provided in the drug dispensing apparatus 2, but some or all of the drugs are provided in the general-purpose cassettes (B-type cassettes 15), desired drugs are discharged from the fixed cassettes (A-type cassettes 13) and the general-purpose cassettes (B-type cassettes 15) and packed for each administration.

When some of drugs included in prescription data are not provided in the drug dispensing apparatus 2, the general-purpose cassette (B-type cassette 15) or the manual distribution portion 6 is used.

When the general-purpose cassette (B-type cassette 15) is used, a drug bottle included in the prescription is searched, and the drugs are filled into the general-purpose cassette (B-type cassette 15). At this time, a barcode, a two-dimensional code, or the like attached to the drug bottle is read with a code reader and recorded. Further, information as to an operator who has performed the filling is recorded.

When the manual distribution portion 6 is used, a drug bottle included in the prescription is searched, and a predetermined number of drugs are charged into the drug charging portions 33 of the manual distribution portion 6 in accordance with the prescription.

Then, bottoms of the drug charging portions 33 open one after another, and the drugs provided in the drug charging portions 33 are caused to fall for each drug charging portion 33 and delivered to the drug packing portion 8 at a lower part.

Also at this time, a barcode, a two-dimensional code, or the like attached to the drug bottle is read with a code reader and recorded. Further, information as to an operator who has performed the manual distribution is recorded.

Next, the drug inspection assisting apparatus 3 is described.

The drug inspection assisting apparatus 3 is an apparatus for inspecting the number and kinds of drugs to be subjected to inspection. The drug inspection assisting apparatus 3 is capable of inspecting the number and kinds of drugs to be subjected to the inspection that are supplied in a state of being packaged in a packaging paper for each administration, for each package.

As illustrated in FIG. 1, the drug inspection assisting apparatus 3 includes an introducing portion 41 and a display device (operation panel) 42. The introducing portion 41 is provided on a side surface of a housing 40 for introducing the drugs to be subjected to inspection. The display device 42 is provided on a front surface of the housing 40. The drugs are packed with a packaging paper having translucency and are supplied to the drug inspection assisting apparatus 3 in a state of being visible from an outside. Further, the drug inspection assisting apparatus 3 is capable of supplying a packaging bag in a state of a packaging-bag continuous body formed such that a plurality of packaging bags each packing a drug for each administration are continuously provided and sequentially performing inspection of the packaging bags.

Figure 9:
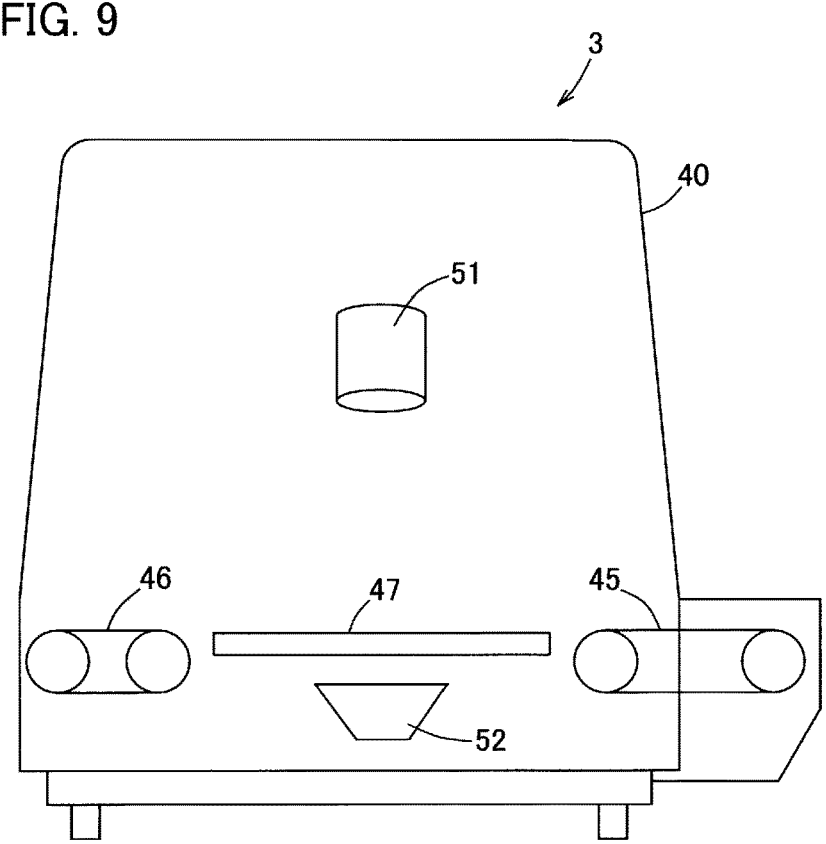
FIG. 9 is a schematic view for illustrating an inside of a drug inspection assisting apparatus.

As illustrated in FIG. 9, conveying means 45 and 46 and an inspection portion 47 are provided inside the drug inspection assisting apparatus 3. Further, the drug inspection assisting apparatus 3 includes a control device 50.

The inspection portion 47 is provided with an image pickup device 51 and an illumination device 52, and images of a packaging bag arranged at the inspection portion 47 and drugs accommodated in the packaging bag are picked up.

The control device 50 is capable of performing processing such as drug inspection processing and supply control. The drug inspection processing is the processing of inspecting whether drugs accommodated in each packaging bag are as prescribed. The supply control is the control of supplying the packaging-bag continuous body including packaging bags arranged continuously in a band-like manner to the drug inspection assisting apparatus 3.

The control device 50 includes a CPU and a memory which are publicly known.

Figure 10:
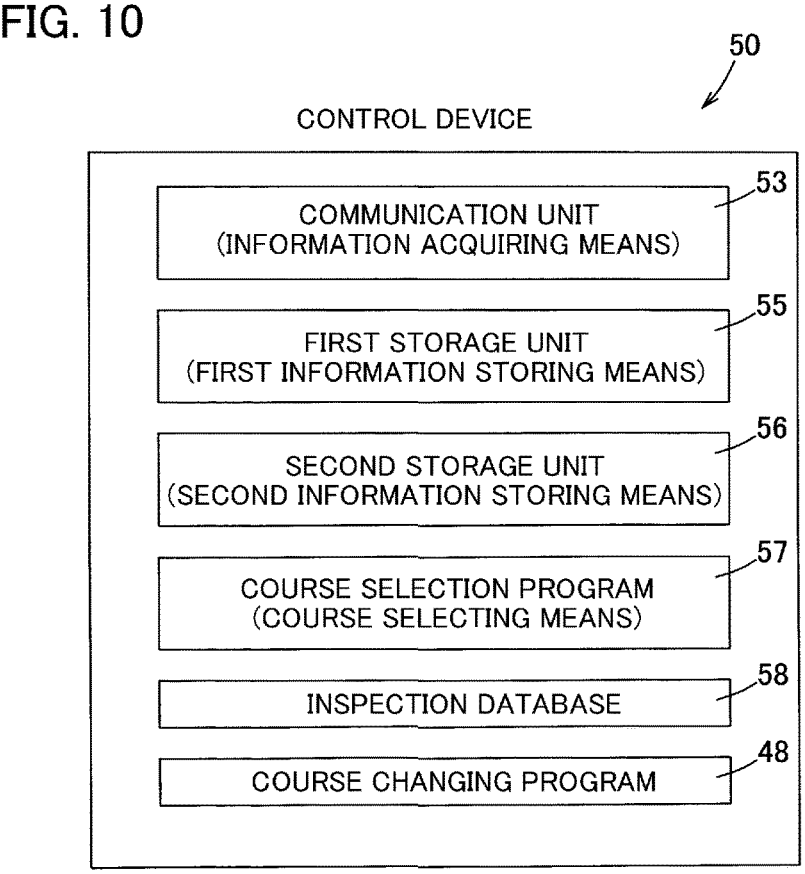
FIG. 10 is a block diagram of a control device of the drug inspection assisting apparatus.

As illustrated in FIG. 10, the control device 50 includes, in terms of function, a communication unit 53, a first storage unit 55, a second storage unit 56, a plan selection program 57, and an inspection database 58.

The communication unit 53 is mutually communicable with the upper apparatus (not shown) and the drug dispensing apparatus 2, and is a means for acquiring prescription information or first information and second information, which are described later, from the upper apparatus and the drug dispensing apparatus 2, that is, functions as an information acquiring means.

The first storage unit 55 stores the first information acquired via the communication unit 53 being the information acquiring means. The second storage unit 56 stores the second information acquired via the communication unit 53 being the information acquiring means.

In the inspection database 58, information regarding drugs required for implementing the inspection is accumulated. Specifically, images of drugs are stored as master images. Further, information for specifying the drugs, such as marks given to the drugs, shapes of the drugs, and dimensions of the drugs are stored.

The drug inspection assisting apparatus 3 includes a plurality of drug inspection means. Further, the drug inspection assisting apparatus 3 is capable of implementing a plurality of drug inspection plans having different accuracies through selective implementation of the drug inspection means.

Specifically, the drug inspection assisting apparatus 3 includes the following drug inspection means.

(1) Mark Inspection

When a solid preparation is a tablet, a fixed-form drug identifier (identifier for specifying a kind of a fixed-form drug) formed on a surface of the tablet by marking or printing is provided. When the solid preparation is a capsule drug, a fixed-form drug identifier formed on a surface of the capsule drug by printing is provided.

The drug inspection assisting apparatus 3 according to this embodiment picks up an image of a solid preparation with the image pickup device 51. Then, the mark is recognized from the image.

The drug inspection assisting apparatus 3 stores, in advance, information acquired by associating each solid preparation and a fixed-form drug identifier formed on each solid preparation. Then, based on the extracted image and the fixed-form drug identifier stored in association with a marked tablet specified in prescription data, determination is made on whether or not the marked tablet having an image thereof picked up is the drug specified in the prescription data. This determination can be made based on a matching ratio between a mark which appears in the extracted image and the fixed-form drug identifier. That is, determination of whether or not the mark of the marked tablet having an image thereof picked up matches the fixed-form drug identifier of the drug specified in the prescription data can be made by a user, for example, through side-by-side display on a screen. In this case, it is preferred that comparison can easily be made by displaying drug data such as a drug name, a picture, and the like. It is more preferred that, when the matching ratio is low, notification of this fact be made through, for example, a change in display color.

(2) Shape Inspection

The control device 50 includes the inspection database 58 in which images of drugs are accumulated as master images. The control device 50 is capable of implementing an inspection operation of executing processing of matching a master image registered in the inspection database 58 with an image of a drug acquired by the image pickup device 51 (image matching processing) and inspecting whether or not the drugs are packed in the packaging bag as prescribed.

Further, the control device 50 executes determination (similarity determination) of whether or not a drug (similar drug) which is similar to a drug packed in a packaging bag is present in the inspection database 58 through the image matching processing, and can give alert when the similar drug is present. That is, through execution of drug-type verification inspection, drug-type matching determination and similarity determination are implemented.

Further, color can also be compared.

(3) Counting Inspection

The drug inspection assisting apparatus 3 is capable of counting the number of solid drugs in each packaging bag. Then, an inspection operation of inspecting whether or not a number of drugs as prescribed is packed in the packaging bag can be performed.

Further, the drug inspection assisting apparatus 3 is capable of performing a total inspection and a sampling inspection. The total inspection is a method of inspecting solid drugs in all of the packaging bags. The sampling inspection is a method of inspecting solid drugs in packaging bags located at specific positions such as a head, a middle, and the last of the packaging bags which are connected to one another in a band-like shape.

With the drug inspection assisting apparatus 3 according to this embodiment, drug inspection plans having different accuracies can be implemented through suitable selection of the drug inspection means.

Selection of the plan is optional, and an enormous number of possible combinations are given. For example, it is conceivable to enable implementation of three kinds of inspection plans, that is, an upper-grade inspection plan, a middle-grade inspection plan, and a simple inspection plan.

In the upper-grade inspection plan, for example, for all of the packaging bags, all of the "mark inspection," the "shape inspection," and the "counting inspection" described above are implemented.

In the middle-grade inspection plan, for example, for all of the packaging bags, the "shape inspection" and the "counting inspection" described above are implemented.

In the simple inspection plan, for example, for all of the packaging bags, only the "counting inspection" is implemented.

The drug inspection plans are not limited to those described above. A larger number of drug inspection plans may be set through combination of, for example, an accuracy of the "mark inspection," a wideness of a target medicine to be subjected to the similarity determination in the "shape inspection," and distinction of the total inspection or the sampling inspection.

The drug inspection assisting apparatus 3 according to this embodiment includes a plan selection means for selecting any one of the "upper-grade inspection plan," the "middle-grade inspection plan," and the "simple inspection plan" described above.

Specifically, the plan selection means is achieved with a plan selection program 57 stored in the control device 50.

In this embodiment, the selection of the drug inspection plan is performed based on first information and second information.

Here, the second information is information related to an operator who is involved in collection of drugs. The second information includes information related to an operator who worked on the operation of accommodating the drugs in the drug dispensing apparatus (drug collecting apparatus) 2.

As described above, the drug dispensing apparatus (drug collecting apparatus) 2 includes the A-type cassettes 13 and the B-type cassettes 15. The drugs are filled into those cassettes, and the A-type cassettes 13 and the B-type cassettes 15 in such a state are mounted at predetermined positions.

The second information include information as to an operator who has filled the drugs into the A-type cassettes 13 or the B-type cassettes 15.

Further, the second information includes a qualification of the operator and the amount of experience. The qualification may be a public qualification such as a pharmacist, a doctor, a dentist, a nurse, a medical technologist, or a radiologist, or an authorized qualification authorized by a pharmacy or a hospital. The qualification may be posts such as a person in charge, a chief, a chief clerk, and a section manager.

It is preferred that the qualification of the operator that should be acquired as the second information be information as to whether or not the operator is a pharmacist.

The amount of experience may be a specific number of years of experience, the number of times the drug filling operation has been actually performed, or the number of attending a training session and the like.

Information about an operator who involved in the collection of the drugs is acquired by a communication means (information acquiring means) 53 from the upper apparatus (not shown) or the drug dispensing apparatus 2 and is stored in the second storage unit 56. Further, a qualification of the operator is also acquired from the upper apparatus (not shown) and is stored in the second storage unit 56.

The first information is information related to collection paths of the drugs and devices involved in the collection of the drugs.

The first information includes information as to whether or not the collected drugs have been collected with use of the drug dispensing apparatus (drug collecting apparatus) 2.

Further, when the collected drugs are drugs having been collected with use of the drug dispensing apparatus (drug collecting apparatus) 2, information as to whether or not all of the drugs have been supplied from the drug dispensing apparatus 2 is also included.

Further, the first information includes information as to whether or not the drugs have been collected with use of the manual distribution portion 6, whether all of the drugs have been provided in the A-type cassettes 13, and whether or not the drugs supplied from the B-type cassettes 15 are included.

Further, the first information also includes information as to whether or not the A-type cassettes 13 or the B-type cassettes 15 having been filled with the drugs are those having a locking function.

Briefly, the first information includes the following information.

(i) Whether or not all of the collected drugs have been collected with use of the drug dispensing apparatus 2, and the drug dispensing apparatus 2 has a function of accommodating a plurality of kinds of drugs inside and automatically dispensing desired drugs.

(ii) Whether or not all of the collected drugs have been accommodated in the drug dispensing apparatus 2.

(iii) Whether or not at least part of the collected drugs have been collected with use of the drug dispensing apparatus 2, and the drug dispensing apparatus 2 includes the manual distribution portion 6 so that at least part of the collected drugs have been collected via the manual distribution portion 6.

(iv) Whether or not all of the collected drugs are drugs having been accommodated in the fixed cassette.

(v) Whether or not part or all of the collected drugs pass through the general-purpose cassette, and all of other drugs are drugs having been accommodated in the fixed cassette.

(vi) Whether or not part or all of the collected drugs pass through the manual distribution portion.

(vii) Whether or not the collected drugs have been collected with use of the drug dispensing apparatus 2, and the drug dispensing apparatus 2 has a plurality of drug cassettes mounted thereto and has a function of accommodating a plurality of kinds of drugs inside the drug cassettes and automatically dispensing desired drugs.

(viii) Kind of drug cassette.

For example, the A-type cassette 13, the B-type cassette 15, and the presence or absence of the locking function.

A plan selection program being a plan selection means selects any one of the "upper-grade inspection plan," the "middle-grade inspection plan," and the "simple inspection plan" in accordance with a combination of the first information and the second information described above.

Selection of the drug inspection plan is performed in accordance with a probability of causing a mistake.

When focus is given to the item related to the operator being the second information, an experienced pharmacist is less liable to make a mistake, and filling operations or manual-distribution operations performed by an experienced pharmacist are most reliable.

Operations performed by a less-experienced pharmacist are next most reliable.

It is assumed that operations performed by an experienced operator who does not have a qualification is also as reliable as the operations performed by a less-experienced pharmacist.

Meanwhile, operations performed by an operator who does not have a qualification and is less experienced are less reliable.

Further, when focus is given to the item related to the collection paths of the drugs and/or the devices involved in the collection of the drugs being the first information, the drugs having been discharged from the A-type cassette (fixed cassette) 13L with a lock is the most reliable, and the reliability is reduced in the descending order of the A-type cassette (fixed cassette) 13 without a lock, the semi-variable A-type cassette (fixed cassette) with a lock, the semi-variable A-type cassette (fixed cassette) without a lock, the B-type cassette (general-purpose cassette) 15L with a lock, the B-type cassette (general-purpose cassette) without a lock, and the manual distribution portion 6.

Further, when the B-type cassette 15 is used as the fixed cassette, the reliability is higher than the case in which the B-type cassette 15 is used as the general-purpose cassette.

For example, when the following conditions are satisfied, the possibility of causing a mistake is low, and hence the "simple inspection plan" is selected.
- (a) All of the collected drugs have been supplied from the drug dispensing apparatus 2.
- (b) Further, all of those drugs have been supplied from the A-type cassette 13L with a lock.
- (c) An operator who has filled the drugs into the A-type cassette 13L with a lock is a pharmacist and is well experienced.

In contrast, when the following conditions are satisfied, it cannot be definitely determined that there is no mistake, and hence the "upper-grade inspection plan" is selected.
- (a) All of the collected drugs have been supplied from the drug dispensing apparatus 2.
- (d) Part of the collected drugs include drugs having been collected via the manual distribution portion.
- (e) A person who has performed the manual distribution operation has a qualification of a pharmacist.

For example, when the operator is a novice, a probability of causing a mistake is high, and hence the inspection with the drug inspection assisting apparatus 3 is not suitable. Thus, this fact is displayed on a display device, and visual inspection is performed.

There are a wide variety of combinations of the first information and the second information. Thus, only one example is shown in FIG. 11, and description of individual cases is omitted.

In principle, when a plurality of operators are involved in the collection of the drugs, the drug inspection plan is selected in accordance with the probability of causing a mistake based on an operator who is the most unreliable. For example, when the medicine A, the medicine B, and the medicine C are prescribed, in a case in which the medicine A and the medicine B are filled into the A-type cassettes 13 by the most reliable experienced pharmacist, but the medicine C is filled into the A-type cassette 13 by a novice pharmacist who is less reliable, the drug inspection plan is selected in accordance with the probability that the novice pharmacist causes a mistake.

Similarly, when the collection paths of the collected drugs and the devices involved in the collection are different, the drug inspection plan is selected in accordance with the probability that a mistake occurs in the collection paths and the devices which are the most unreliable.

Then, the drug inspection assisting apparatus 3 automatically implements the selected drug inspection plan.

It is recommended that, before the drug inspection plan is executed, the fact that the drug inspection plan has been selected be displayed to urge confirmation. Further, it is preferred that control which enables the drug inspection plan to be manually changed be employed.

As a result of implementing the drug inspection plan, when the collected drugs are provided as specified by the prescription data, this fact is displayed on the display device (operation panel) 42 illustrated in FIG. 1.

When the drugs are incorrect, or the number of the drugs is incorrect, "NG" is given as an inspection result, and a content indicating the incorrectness is displayed on the display device 42. In such a case, the operator may specify the incorrectness and display it together.

In a case in which drugs whose shape or other record is not present in the inspection database 58 (also referred to as "non-registered drug 21") are prescribed, "NG" is given as an inspection result. It is preferred that the display be distinguished from the "NG" given due to the above-mentioned incorrectness.

Further, similarly, also when a transparent drug is prescribed, "NG" is given as an inspection result. When an image of the transparent drug is picked up with the image pickup device 51, a contour cannot be identified, or an image of a pattern on the back is picked up. Thus, the transparent drug is not suitable for the inspection by the image processing.

Thus, similarly, when the transparent drug is prescribed, "NG" is given as an inspection result. Also in this case, it is preferred that the display be distinguished from the "NG" given due to the above-mentioned incorrectness.

For example, it is preferred that displays such as "An unverified drug is included." or "A transparent drug is included." be displayed, and such description be given also on a journal paper.

Further, the fact that an unverified drug is included or the fact that a transparent drug is included are already known before inspection. Thus, it is preferred that required inspection based on, for example, the number, the shape, and the marks be performed on drugs other than the unverified drugs or transparent drugs.

When unregistered drugs or transparent drugs are prescribed, it is required that visual inspection be performed. When the "NG" is distinguished from that caused by normal error, the inspection operation can be smoothly proceeded, and the effect of preventing the error in the visual inspection can also be expected.

In principle, when both the first information and the second information are the same, the same drug inspection plan is selected. However, the drug inspection plan may be changed in consideration of an elapse of time (the number of inspections).

For example, when a novice person having no qualification filled a drug A into a specified A-type cassette 13, the drug inspection based on the "upper-grade inspection plan" is originally implemented. However, there is envisioned a case in which, as a result of discharging drugs from the same A-type cassette 13 a plurality of times as prescriptions for different patients and performing the drug inspection based on the "upper-grade inspection plan," error is not found.

In such a case, it is less likely to be assumed that there was any error in filling the drugs into the A-type cassette 13. In such a case, the rank of the inspection accuracy may be lowered, and, for example, the "middle-grade inspection plan" may be performed.

Further, as described above, a portable reading terminal is used at the time of selecting a drug bottle from, for example, a shelf. When this operation has not been performed, the rank of the inspection accuracy may be raised, and as a result of discharging drugs from the same A-type cassette 13 a plurality of times as prescriptions for different patients and performing the drug inspection and no error is found, the rank of the inspection accuracy may be lowered.

In the drug inspection assisting apparatus 3 according to this embodiment, as described above, a plan changing control program 48 for lowering the rank of the inspection accuracy is built in the control device 50.

In accordance with the example described above, certain specific information of "novice person without qualification" being a certain operator is included in the second information.

Further, the first information includes certain specific information that the drugs pass through the specific A-type cassette 13.

In this case, the "upper-grade inspection plan" is implemented.

However, after that, when the "upper-grade inspection plan" is repeated a plurality of times, that is, two or three times based on the first information and the second information including the certain specific information described above, and there is no error in the collected drugs in all of the implementations, the accuracy of the drug inspection plan is lowered, and the "middle-grade inspection plan" is performed.

Further, depending on whether or not drugs having similar shapes or the like are included in the prescribed drugs, the rank of the inspection accuracy may be changed.

For example, when drugs having a similar shape or the like are present, it may be expected that the completeness cannot be ensured with only the shape inspection. In such a case, the rank of the inspection accuracy may be raised, and the mark inspection may be implemented.

For example, when drugs which are different but have a similar shape are present in images of drugs in the inspection database 58, for example, flags may be given to this data so that the data can easily be extracted. Among the prescribed drugs, when drugs having a similar shape are not present in a certain verification target drug group, the shape inspection is performed. When drugs having a similar shape are present in the verification target drug group, the rank of the inspection accuracy is raised, and the mark inspection is implemented.

The verification target drug group includes, for example, drugs having the same administration timing. The verification target drug group may be freely selected. For example, the range may be extended to the same prescription, and the target may be further extended to the drug provided in the drug dispensing apparatus 2, or to the drugs owned by a pharmacy or the like.

The embodiment described above is directed to the drug inspection assisting system 1 including the combination of the drug dispensing apparatus (drug collecting apparatus) 2 and the drug inspection assisting apparatus 3, and the drugs are inspected after being charged into packaging bags. However, the drug inspection assisting apparatus 3 may be used for inspecting the drugs collected before packing.

Further, the drug inspection assisting apparatus 3 may be used for inspection of drugs collected by manual operation.

REFERENCE SIGNS LIST

1; drug inspection assisting system, 2; drug dispensing apparatus (drug collecting apparatus), 3; drug inspection assisting apparatus, 5; cassette mounting portion, 6; manual distribution portion, 10; fixed-cassette mounting area, 11; general-purpose-cassette mounting area, 13; A-type cassette, 13L; A-type cassette with a lock, 15; B-type cassette, 15L; B-type cassette with a lock, 33; drug charging portion, 47; inspection portion, 50; control device, 53; communication means, 57; plan selection program (plan selection means), 58; inspection database, 71; lid member, 75; cassette placement portion

The invention claimed is:

1. A drug inspection assisting apparatus for assisting an inspection of drugs collected by a drug collecting apparatus and/or by a manual operation, comprising:
   a control device;
   an image pickup device; and
   a communication unit for acquiring first information and second information,
      the first information being information related to collection paths of the drugs and/or devices involved in collection of the drugs,
      the second information being information related to an operator who is involved in the collection of the drugs,
   wherein the control device implements a plurality of drug inspection plans having different accuracies, the plurality of drug inspection plans including a first drug inspection plan that inspects kinds of the drugs, and a second drug inspection plan that inspects a number of the drugs, wherein at least one of the first drug inspection plan or the second drug inspection plan includes picking up an image of the drugs packed in a packaging bag by the image pickup device,
   wherein the control device causes the communication unit to acquire the first information and the second information,
   wherein the control device selects one drug inspection plan of the plurality of drug inspection plans based on the first information and the second information, and
   wherein the control device implements the selected drug inspection plan.

2. The drug inspection assisting apparatus according to claim 1, wherein the drug collecting apparatus has a function of accommodating a plurality of kinds of drugs inside and automatically dispensing desired drugs, and the second information includes information related to an operator who is involved in an operation of accommodating the drugs into the drug collecting apparatus.

3. The drug inspection assisting apparatus according to claim 1, wherein the second information includes at least one of information (A1) and information (A2), where:
   (A1) presence or absence of a public qualification; and
   (A2) an amount of experience.

4. The drug inspection assisting apparatus according to claim 1, wherein the first information includes information (B1), where:
   (B1) whether or not all of the collected drugs have been collected with use of a drug collecting apparatus, and the drug correcting apparatus has a function of accommodating a plurality of kinds of drugs inside and automatically dispensing desired drugs.

5. The drug inspection assisting apparatus according to claim 4, wherein the first information includes information (C1), where:
   (C1) whether or not all of the collected drugs have been accommodated in the drug collecting apparatus.

6. The drug inspection assisting apparatus according to claim 1, wherein the first information includes information (D1), where:
   (D1) whether or not at least part of the collected drugs have been collected with use of the drug collecting apparatus, and the drug collecting apparatus includes a manual distribution portion, and the manual distribution portion includes a plurality of drug charging portions so that a predetermined number of drugs are charged into the drug charging portion by a manual operation of an operator, and at least part of the collected drugs are drugs having been collected via the manual distribution portion.

7. The drug inspection assisting apparatus according to claim 1,
wherein the drug collecting apparatus includes a manual distribution portion and a plurality of drug cassette mounting portions,
wherein the manual distribution portion includes a plurality of drug charging portions, and a predetermined number of drugs are charged into the drug charging portions by manual operation of an operator,
wherein at least two kinds of drug cassettes are mounted to the drug cassette mounting portion, and at least one kind of the drug cassette is a fixed cassette to be used exclusively for a certain drug, and at least another one kind of the drug cassette is a general-purpose cassette to be used for a plurality of kinds of drugs, and
wherein the first information includes distinctions (E1) to (G1), where:
(E1) all of the collected drugs are drugs having been accommodated in the fixed cassette;
(F1) part or all of the collected drugs pass through the general-purpose cassette, and all of other drugs have been accommodated in the fixed cassette; and
(G1) part or all of the collected drugs pass through the manual distribution portion.

8. The drug inspection assisting apparatus according to claim 7, wherein the first information includes information (I1), where:
(I1) structural distinction of the drug cassettes.

9. The drug inspection assisting apparatus according to claim 8, wherein the drug cassettes include a drug charging portion configured to charge drugs, and the structural distinction includes the drug charging portion which is capable of being locked and the drug charging portion which is incapable of being locked.

10. The drug inspection assisting apparatus according to claim 8, wherein the structural distinction includes the drug cassette adaptable to a large number of kinds of drugs and the drug cassette adaptable to a small number of kinds of drugs.

11. The drug inspection assisting apparatus according to claim 7, wherein the first information includes information (J1), where:
(J1) usage distinction of the drug cassette.

12. The drug inspection assisting apparatus according to claim 11, wherein the usage distinction includes information that the drug cassettes include a fixed cassette to be used exclusively for a certain drug and a general-purpose cassette to be used for a plurality of kinds of drugs.

13. The drug inspection assisting apparatus according to claim 1, wherein the first information includes information as to whether a requirement (H1) is satisfied, where:
(H1) all of the collected drugs have been collected with use of the drug collecting apparatus, and the drug collecting apparatus has a plurality of drug cassettes mounted thereto and has a function of accommodating a plurality of kinds of drugs inside the drug cassettes and automatically dispensing desired drugs.

14. The drug inspection assisting apparatus according to claim 1, wherein information acquired by the communication unit includes certain specific information, and a certain drug inspection plan is selected based on the information, thus the drug inspection plan is implemented, and
wherein, after that, the same drug inspection plan is selected a plurality of times based on the information including the specific information, and the drug inspection plan is implemented a plurality of times, and as a result, under a condition in which no error has been found in the collected drugs in all of the implementations, plan change control for correcting the accuracy of the drug inspection plan downward is implemented.

15. A drug inspection assisting system, comprising:
the drug inspection assisting apparatus according to claim 1; and
a drug collecting apparatus,
wherein the drug collecting apparatus includes a manual distribution portion and a plurality of drug cassette mounting portions,
wherein the manual distribution portion includes a plurality of drug charging portions, and a predetermined number of drugs are charged into the drug charging portions by manual operation of an operator,
wherein at least two kinds of drug cassettes are mounted to the drug cassette mounting portion, and at least one kind of the drug cassette is a fixed cassette to be used exclusively for a certain drug, and at least another one kind of the drug cassette is a general-purpose cassette to be used for a plurality of kinds of drugs.

16. The drug inspection assisting apparatus according to claim 1, wherein the control device is configured to determine whether the kinds of the drugs packed in the packaging bag are as prescribed based on the image of the drugs packed in the packaging bag that is acquired by the image pickup device.

17. The drug inspection assisting apparatus according to claim 1, wherein the control device implements the first drug inspection plan and the second drug inspection plan.

18. A drug inspection assisting apparatus for assisting an inspection of drugs collected by a drug collecting apparatus and/or by a manual operation, comprising:
a control device;
an image pickup device; and
a communication unit for acquiring first information,
the first information being information related to collection paths of the drugs and/or devices involved in collection of the drugs; and
wherein the control device implements a plurality of drug inspection plans having different accuracies, the plurality of drug inspection plans includes a first drug inspection plan that inspects kinds of the drugs, and a second inspection plan that inspects a number of the drugs, wherein at least one of the first drug inspection plan or the second drug inspection plan includes picking up an image of the drugs packed in a packaging bag by the image pickup device,
wherein the control device causes the communication unit to acquire the first information,
wherein the control device selects one drug inspection plan from the plurality of drug inspection plans based on the first information, and
wherein the control device implements the selected drug inspection plan.

19. The drug inspection assisting apparatus according to claim 18, wherein the control device implements the first drug inspection plan and the second drug inspection plan.

20. A drug inspection assisting method for assisting, with use of a drug inspection assisting apparatus, an inspection of drugs collected by a drug collecting apparatus and/or by a manual operation of an operator, the drug inspecting assisting apparatus including:
an image pickup device; and
a communication unit configured to acquire a first unit of information and a second unit of information, wherein the first unit of information is related to collection paths of the drugs and/or devices involved in collection of the drugs, and wherein the second unit of information is related to an operator who is involved in the collection of the drugs, wherein the method includes:
- implementing a plurality of drug inspection plans having different accuracies, wherein the plurality of drug inspection plans includes a first drug inspection plan that inspects kinds of the drugs, and a second drug inspection plan that inspects a number of the drug, wherein at least one of the first drug inspection plan or the second drug inspection plan includes picking up an image of the drugs packed in a packaging bag by the image pickup device;
- acquiring the first unit of information and the second unit of information by the communication unit;
- selecting one drug inspection plan from the plurality of drug inspection plans based on the first unit of information and the second unit of information; and
- implementing the selected drug inspection plan.

\* \* \* \* \*